United States Patent
Yamada et al.

(10) Patent No.: US 10,695,082 B2
(45) Date of Patent: Jun. 30, 2020

(54) ULTRASONIC TREATMENT INSTRUMENT FOR ARTICULATIONS, AND TREATMENT METHOD THEREOF

(71) Applicant: OLYMPUS CORPORATION, Hachioji-shi, Tokyo (JP)

(72) Inventors: Masashi Yamada, Sagamihara (JP); Yasuo Tanigami, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 105 days.

(21) Appl. No.: 16/146,080

(22) Filed: Sep. 28, 2018

(65) Prior Publication Data
US 2019/0029710 A1    Jan. 31, 2019

Related U.S. Application Data (63) Continuation of application No. PCT/JP2016/059911, filed on Mar. 28, 2016.

(51) Int. Cl.
*A61B 17/32* (2006.01)
*A61B 17/16* (2006.01)
A61B 17/00 (2006.01)

(52) U.S. Cl.
CPC .. *A61B 17/320068* (2013.01); *A61B 17/1659* (2013.01); *A61B 2017/00017* (2013.01); *A61B 2017/00973* (2013.01); *A61B 2017/320004* (2013.01); *A61B 2017/320072* (2013.01); *A61B 2017/320082* (2017.08); *A61B 2017/320098* (2017.08)

(58) Field of Classification Search
CPC ............. A61B 17/320068; A61B 17/1659
See application file for complete search history.

(56) References Cited

U.S. PATENT DOCUMENTS 2,714,890 A * 8/1955 Vang ............... A61B 17/320068
606/169
5,188,102 A * 2/1993 Idemoto ......... A61B 17/320068
604/22
(Continued)

FOREIGN PATENT DOCUMENTS

EP    2 057 960 A1    5/2009
JP    2003-526415 A    9/2003
(Continued)

OTHER PUBLICATIONS

Oct. 29, 2019 Office Action issued in Japanese Patent Application No. 2018-507838.
(Continued)

*Primary Examiner* — Christian A Sevilla
(74) *Attorney, Agent, or Firm* — Oliff PLC (57) ABSTRACT

The ultrasonic treatment instrument for articulations according to the embodiment of the present invention includes, at the distal end of the probe, the treatment section which performs a desired treatment on the treated target part. The treatment portion is provided with an edge which extends in a direction crossing, or a direction parallel to, the longitudinal direction of the probe; a first ultrasonic transducer which generates ultrasonic vibration in a direction crossing the edge; and a second ultrasonic transducer which generates ultrasonic vibration in a direction parallel, to the edge.

5 Claims, 9 Drawing Sheets

(56) References Cited

U.S. PATENT DOCUMENTS

| | | | |
|---|---|---|---|
| 6,402,769 B1 | 6/2002 | Boukhny | |
| 6,423,082 B1 * | 7/2002 | Houser | A61B 17/320068 606/169 |
| 6,562,032 B1 * | 5/2003 | Ellman | A61B 17/320068 606/41 |
| 7,476,233 B1 * | 1/2009 | Wiener | A61B 17/320068 606/169 |
| 2002/0077645 A1 * | 6/2002 | Wiener | A61B 17/320068 606/169 |
| 2005/0021065 A1 | 1/2005 | Yamada et al. | |
| 2006/0211943 A1 * | 9/2006 | Beaupre | A61B 17/320068 600/471 |
| 2008/0234710 A1 * | 9/2008 | Neurohr | A61B 17/320068 606/169 |

FOREIGN PATENT DOCUMENTS

| | | | |
|---|---|---|---|
| JP | 2005-040222 A | 2/2005 | |
| JP | 2015-43879 A | 3/2015 | |

OTHER PUBLICATIONS

Jun. 21, 2016 Search Report issued in International Patent Application No. PCT/JP2016/059911.

Oct. 2, 2018 International Preliminary Report on Patentability issued in International Patent Application No. PCT/JP2016/059911.

Jul. 9, 2019 Office Action issued in Japanese Patent Application No. 2018-507838.

\* cited by examiner

ULTRASONIC TREATMENT INSTRUMENT FOR ARTICULATIONS, AND TREATMENT METHOD THEREOF

CROSS-REFERENCE TO RELATED APPLICATIONS

This is a Continuation Application of PCT Application No. PCT/JP2016/059911, filed Mar. 28, 2016, the entire contents of which are incorporated herein by references.

BACKGROUND OF THE INVENTION

1. Field of the Invention

The present invention relates to an ultrasonic treatment instrument for articulations, which performs both mechanical abrasion and dissolutive abrasion by heat by ultrasonic vibrations of different vibrations, and a treatment method thereof.

2. Description of the Related Art

In general, a cartilage is formed of protein (collagen) as a main component, and is soft and elastic. Abrasion of a cartilage in a surgical treatment is performed by using a treatment instrument such as an electric scalpel. In addition, in recent years, it has been reported that, with use of an ultrasonic treatment instrument, a surgical treatment such as abrasion can be performed not only on a biological tissue, but also on a treated target part such as a bone. Normally, it is assumed that even if vibration is applied to a cartilage, the vibration is absorbed in the cartilage by elastic force, and it is thought that a mechanical abrasion function by ultrasonic vibration does not occur.

For example, if an ultrasonic treatment instrument, which generates ultrasonic vibration along with heat generation, as disclosed in Jpn. Pat. Appln. KOKAI Publication No. 2015-43879 (patent document 1), is used, an abrasion treatment can be performed on all parts of bones (cortical bones and cancellous bones), such as a cartilage and a subcartilaginous bone, and biological tissues. On the other hand, since the abrasion treatment can be performed on all parts, it is not easy to realize an abrasion treatment for cutting apart a biological tissue and a cartilage, and cutting apart a cartilage and a subcartilaginous bone. For example, in a surgery of articulations, it is necessary to cut and divide a cartilage, a synovium and a subcartilaginous bone. In a cutting-and-opening treatment and an abrasion treatment, it is important for a surgeon to ascertain cutting and dividing of parts so that an underlying part may not be damaged as much as possible, and the surgeon is required to have experience and skill.

The present invention provides an ultrasonic treatment instrument for articulations, and a treatment method thereof, the ultrasonic treatment instrument for articulations including a treatment section which switchably generates longitudinal vibration and twisting vibration, and can select a bone abrasion mode which performs mechanical abrasion and a cartilage abrasion mode which perform dissolutive abrasion by generating heat.

BRIEF SUMMARY OF THE INVENTION

According to an embodiment of the present invention, there is provided an ultrasonic treatment system for articulations, comprising an ultrasonic treatment instrument configured to perform a treatment on an articulation by using ultrasonic vibration, and a driving control device configured to control driving by the ultrasonic vibration, the ultrasonic treatment instrument comprising: a probe including a distal portion and a proximal portion and configured to transmit ultrasonic vibration, the probe being configured such that a length from the distal portion to the proximal portion is set to be equal to an integral multiple of ½ wavelength which is a first wavelength of one preset ultrasonic vibration, and a slit formed at a position of ½ wavelength from the distal portion; a treatment section provided at the distal portion of the probe and configured to perform a treatment on a treated target part; and a first ultrasonic transducer configured to transmit ultrasonic vibration to the treatment section, and the driving control device comprising: a driving control unit configured to transmit to the first ultrasonic transducer a driving signal which causes the first ultrasonic transducer to generate ultrasonic vibration with at least two different frequencies, the driving control unit being configured to cause the probe to generate longitudinal vibration by applying to the first ultrasonic transducer a driving signal of an oscillation frequency of an integral multiple of the first wavelength, and configured to cause the probe to generate twisting vibration by applying to the first ultrasonic transducer a driving signal of an oscillation frequency other than the oscillation frequency of the integral multiple of the first wavelength.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the present invention will be described in detail with reference to the accompanying drawings.

An ultrasonic treatment instrument of the present embodiment includes a probe which includes, at a distal end thereof, a treatment section. The treatment section can perform a surgical treatment on a desired treated target part by ultrasonic vibrations in different directions, and can perform both dissolutive abrasion using heat by ultrasonic vibration, and mechanical abrasion by using ultrasonic vibration. The treatment section switchably performs a normal abrasion mode which abrades a biological tissue, a cartilage and a bone which are treated target parts, and a cartilage abrasion mode which reduces the abrasion of a bone by reducing the function of mechanical abrasion, performs dissolutive abrasion using generated heat by ultrasonic vibration and frictional heat, and abrades a cartilage among the treated target parts.

The term "mechanical abrasion" here means that an edge (to be described later) crushes a treated target part by ultrasonic vibration by being applied to the treated target part in the state in which the edge beats, pushes, pulls and rotates the treated target part by ultrasonic vibration. In the description below, the mechanical abrasion is referred to as "mechanical abrasion" or "crushing abrasion". Besides, in some cases, since the mechanical abrasion beats the treated target part by the probe being swung by the amplitude of ultrasonic vibration, the mechanical abrasion is referred to as "hammering effect" or "hammering function".

The abrasion on a cartilage occurs by the treatment section being pushed on the cartilage, and by locally heating the cartilage up to a temperature at which the cartilage is dissolved. In the present embodiment, a cartilage abrasion portion of the treatment section, when applied to the cartilage in the state in which ultrasonic vibration is added, generates heat as heat of the treatment section itself by the vibration and generates frictional heat at a time when the treatment section is applied to the treated target part, and the temperature of the cartilage is raised up to a proper temperature at which the cartilage is dissolved. In addition, as the proper temperature, the temperature of the cartilage abrasion portion is set such that the temperature of the cartilage portion of the treated target that is put in contact with the cartilage abrasion portion rises up to a range of 45° C. to 220° C., more preferably 120° C. to 160° C.

First Embodiment

Figure 1:
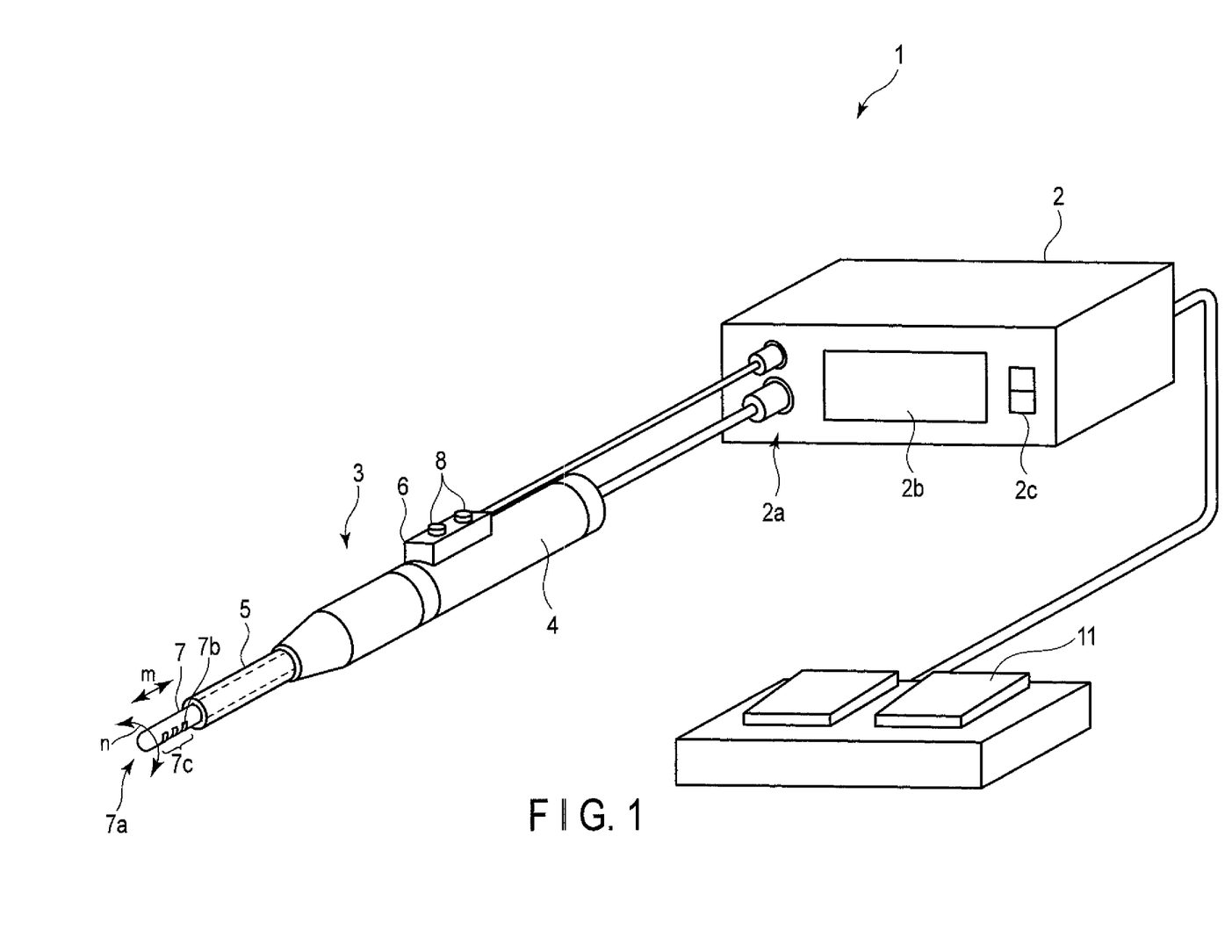
FIG. 1 is a view illustrating an example of an external appearance configuration of an ultrasonic treatment instrument according to a first embodiment.
Figure 2:
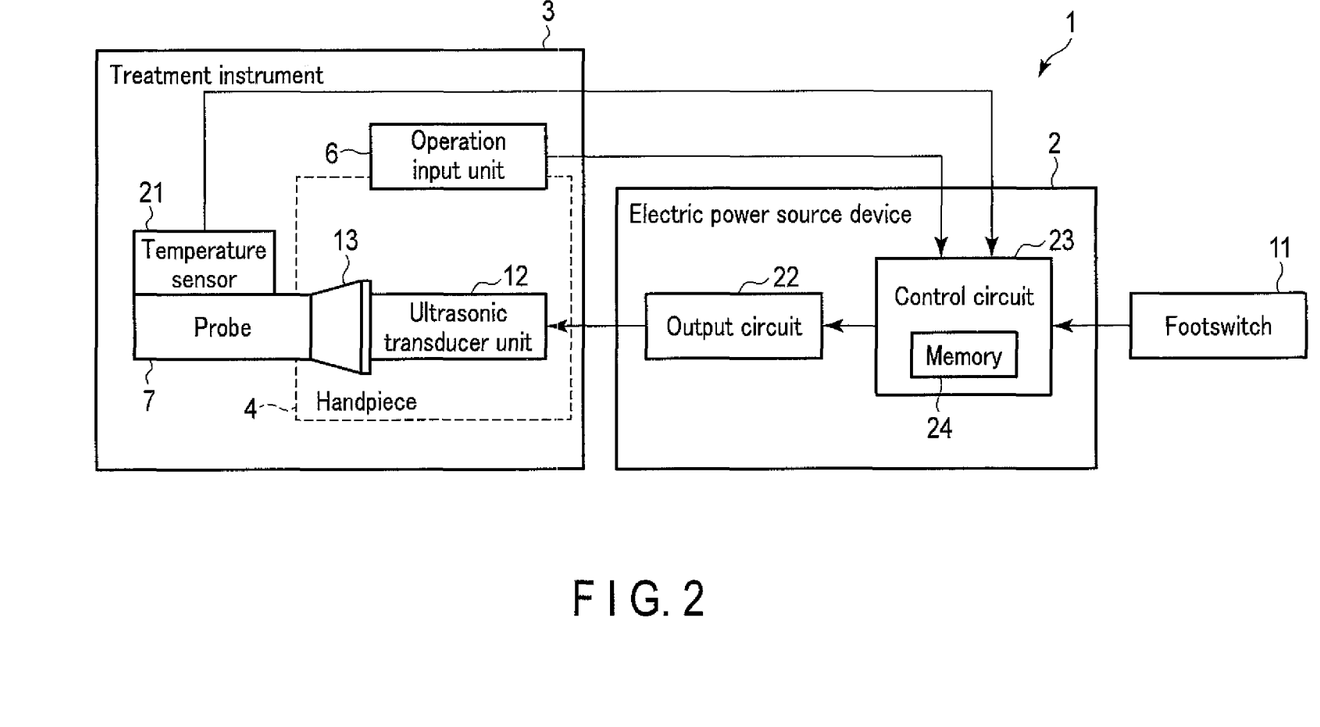
FIG. 2 is a block diagram illustrating a main configuration of the ultrasonic treatment instrument according to the first embodiment.

Referring to FIG. 1, an ultrasonic treatment instrument for articulations according to a first embodiment of the present invention will be described. FIG. 1 is a view illustrating an example of an external appearance configuration of the ultrasonic treatment instrument for articulations (hereinafter referred to as "ultrasonic treatment instrument") according to the first embodiment. FIG. 2 is a block diagram illustrating a main configuration of the ultrasonic treatment instrument.

The ultrasonic treatment instrument 1 includes a treatment instrument 3 for performing, by ultrasonic vibration, an abrasion treatment or an opening-and-cutting treatment on a treated target part such as a biological tissue, a cartilage, a bone (subcartilaginous bone), etc.; an electric power source device 2 which supplies driving electric power to the treatment instrument 3; and a footswitch 11 having the same function as an operation input unit 6 (to be described later). Note that in the ultrasonic treatment instrument 1 of the present embodiment, a minimum system configuration for describing the gist of the technical features is illustrated, and it is assumed that structural parts, which are not illustrated but are generally used as an ultrasonic surgery system, are provided.

The treatment instrument 3 includes a cylindrical handpiece 4 which a surgeon holds; an elongated probe 7 which extends from one end of the handpiece 4; a sheath 5 formed in a manner to cover the periphery of the probe 7; an operation input unit 6 for issuing an instruction; and a temperature sensor 21 which measures the temperature of a treatment section 7a (to be described later) of the probe 7. The handpiece 4 is connected to the electric power source device 2 by a cable, and driving electric power is supplied or a control signal is communicated.

An ultrasonic transducer unit 12 is provided in the inside of the handpiece 4. The ultrasonic transducer unit 12 is acoustically coupled to the probe 7 via a horn section 13. The ultrasonic transducer unit 12 is supplied with driving electric power from the electric power source device 2, and generates ultrasonic vibration. The generated ultrasonic vibration is propagated to the probe 7. The probe 7 is formed of a metallic material, such as a titanium alloy, which is capable of sterilization treatment if the probe 7 is repeatedly used, and has resistance to corrosion. Since the treatment section 7a abrades a bone of a treated target part in a manner to crush the bone, the treatment section 7a needs to have a higher rigidity than the bone of the treated target, and to have durability to vibration.

The probe 7 is covered with the sheath 5 such that a distal portion, which serves as the treatment section 7a, is exposed. The treatment section 7a vibrates by the ultrasonic vibration which is propagated from the ultrasonic transducer unit 12. Although FIG. 1 illustrates a form of the sheath 5 that exposes a surface of an end portion of the probe 7, too, which is on the side opposite to the treatment section 7a, the sheath 5 may have such a form as to expose only an edge portion 7*c* of the treatment section 7*a* and covers the other portion. As will be described later, the ultrasonic transducer unit 12 includes two ultrasonic transducers 26 and 27 having different directions of vibration. The ultrasonic transducer unit 12 can cause the treatment section 7*a* to switchably generate longitudinal vibration, which is vibration along a longitudinal direction m of the probe 7, and twisting vibration in a crossing direction n which crosses the longitudinal direction m. In the present embodiment, a crossing direction, which is perpendicular to the longitudinal direction m, will be described by way of example. The handpiece 4 is provided with the operation input unit 6 on a side surface thereof, which serves as a grasping surface. This operation input unit 6 includes a plurality of operation switches 8 for instructing the driving of the ultrasonic transducer unit 12. The operation switches 8 include not only a switch for an ON/OFF operation of driving electric power which is supplied to the ultrasonic transducer unit 12, but also a change-over switch (switching portion) for performing an operation for switching between a cartilage abrasion mode for dissolutive abrasion and a normal abrasion mode for perming both dissolutive abrasion and mechanical abrasion. In the present embodiment, the footswitch 11 has the same function as the operation input unit 6.

The electric power source device 2 is composed of an output circuit 22 which supplies driving electric power to the ultrasonic transducer unit 12, and a control circuit 23 which controls the output circuit 22. The output circuit 22 is electrically connected to the ultrasonic transducer unit 12 in the handpiece 4 over a cable or the like, and supplies driving electric power for driving the ultrasonic transducer unit 12. The control circuit 23 is composed of a processing circuit which includes therein a memory 24 and has an arithmetic processing function. The control circuit 23 controls the driving electric power which is output from the output circuit 22, in accordance with an instruction (ON/OFF instruction or mode select instruction, etc.) which is input from the operation input unit 6 or footswitch 11, and a detection signal from the temperature sensor 21.

The control circuit 23 executes control by effecting switching between the normal abrasion mode and the cartilage abrasion mode in accordance with the instruction from the operation input unit 6. When the cartilage abrasion mode is set, the control circuit 23 controls, based on the detection signal of the temperature sensor 21, the value of supplied driving electric power such that the temperature rises up to the above-described temperature range (the range of 45° C. to 220° C., more preferably 120° C. to 160° C.). Note that when temperature control at the time of the cartilage abrasion mode is executed, this can be realized even with a configuration without the temperature sensor 21. For example, when a manufacturing error of the probe 7 is small and the characteristics thereof are stable, the temperature control at the time of the cartilage abrasion mode can be executed by parameter setting.

In this case, a pushing weight is set at a fixed value, and such amplitude values of ultrasonic vibration as to set the temperature of the cartilage at a specified temperature in the range of 45° C. to 220° C., more preferably 120° C. to 160° C., are calculated by a plurality of times of actual measurement. An averaged amplitude value is prestored as a control parameter in the memory 24 of the control circuit 23. At the time of use in the cartilage abrasion mode, the control circuit 23 reads out from the memory 24 the control parameter which realizes the required set temperature, and executes ultrasonic vibration based on this control parameter.

Figure 3A:
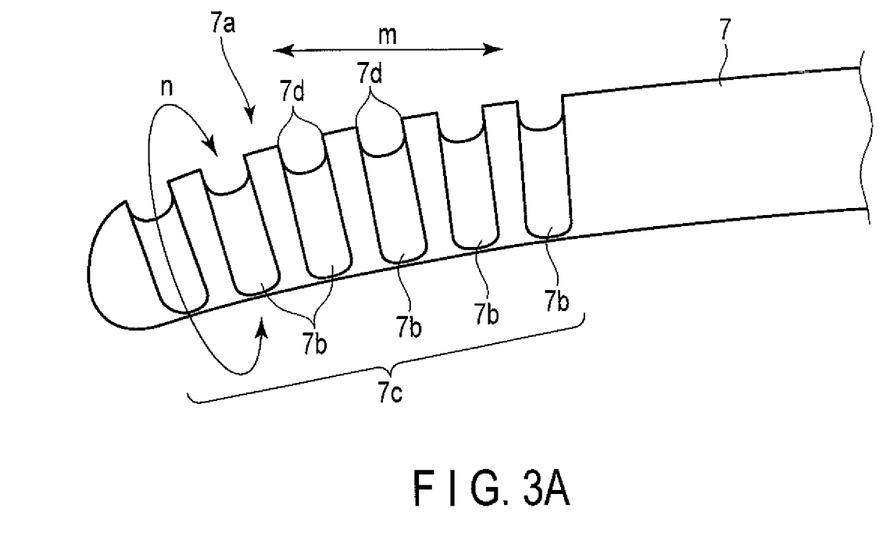
FIG. 3A is a view illustrating a conceptual external appearance configuration of a treatment section, as viewed from a lateral surface side, which is provided in a probe in the first embodiment.
Figure 3B:
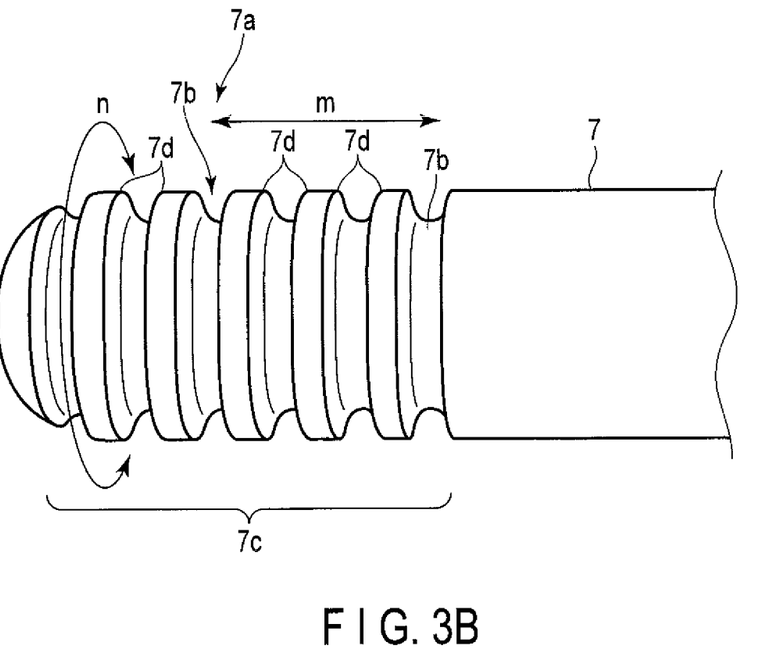
FIG. 3B is a view illustrating a conceptual external appearance configuration of the treatment section, as viewed from a front surface side, which is provided in the probe in the first embodiment.

FIG. 3A and FIG. 3B illustrate an external appearance configuration of the treatment section 7*a* provided on the distal side of the probe 7. The treatment section 7*a* is provided with an edge portion 7*c* including an edge 7*d* which is formed by at least one groove 7*b* in a range of contact with the treated target part. The groove 7*b* extends in a crossing direction (circumferential direction) n which is perpendicular to the longitudinal direction m of the probe 7, and is formed in a U shape with both side faces opened. The groove 7*b* is trenched substantially perpendicularly from a smooth curved surface of the probe 7 to a depth reaching at least the center axis in the longitudinal direction. The width between the edges 7*a* (i.e. the distance between both opposed walls of the groove 7*b*) and the depth thereof can properly be set. Needless to say, the shape of the groove 7*b* is not limited, and it should suffice if an angular portion (edge 7*d*) is provided on at least the surface of the probe 7. Accordingly, in the present embodiment, although the edges 7*d* are formed by the groove (recess portion) 7*b*, the edges 7*d* may be formed by a projection which protrudes in a projecting shape.

When the edge portions 7*c* are formed by plural grooves 7*b*, as illustrated in FIG. 3A, the grooves 7*b* are arranged at regular intervals or at arbitrary intervals along the longitudinal direction m. Note that the arrangement at arbitrary intervals may be properly set at the time of manufacture, and may be, for example, such an arrangement at different intervals that the plural grooves 7*b* are arranged with smaller intervals between edges 7*d* on the central side, and with greater intervals between edges 7*d* on both outer sides. When the range of contact with the treated target part is specified, in order to better obtain the effect of beating the treated target part, i.e. the hammering effect, a greater effect can easily be obtained by narrowing, rather than widening, the intervals between the edges 7*d*, since this increases the surface area of the probe 7, i.e. the area for beating. However, if the intervals between the edges 7*d* are too narrow, the function of abrasion or crushing by the edges 7*d* decreases.

Figure 5:
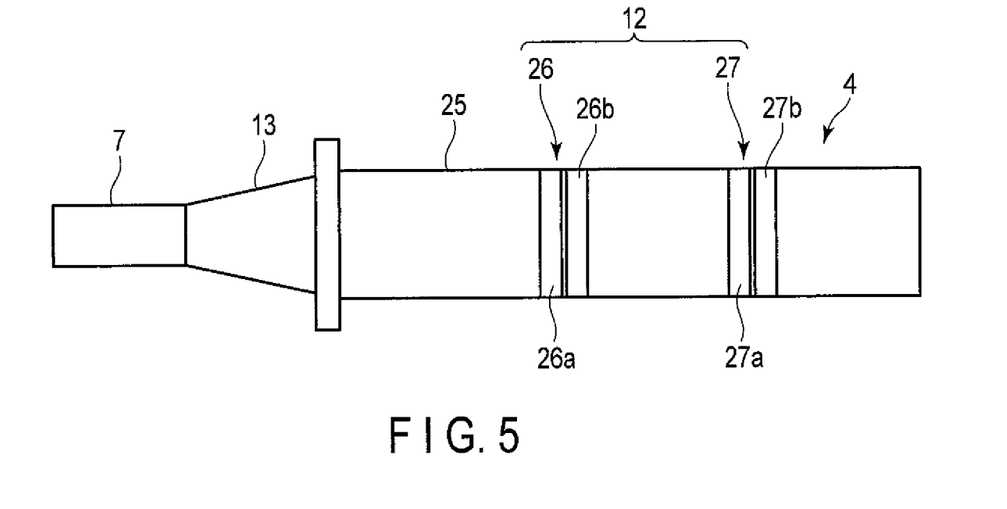
FIG. 5 is a view which conceptually illustrates a configuration example of an ultrasonic transducer unit of a handpiece.
Figure 6:
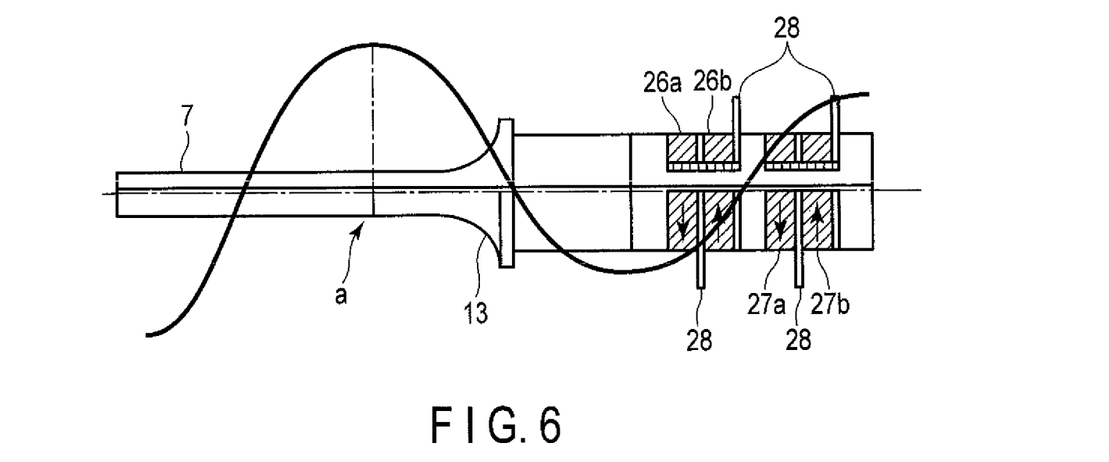
FIG. 6 is a view illustrating a concept for explaining the generation of ultrasonic vibration by an ultrasonic transducer of the handpiece.
Figure 7A:
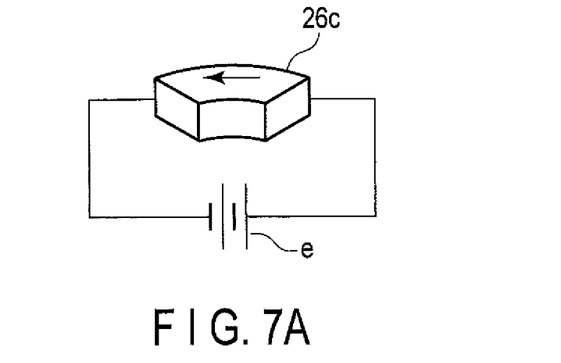
FIG. 7A is a view for explaining the generation of vibration by polarization of an ultrasonic transducer.
Figure 7B:
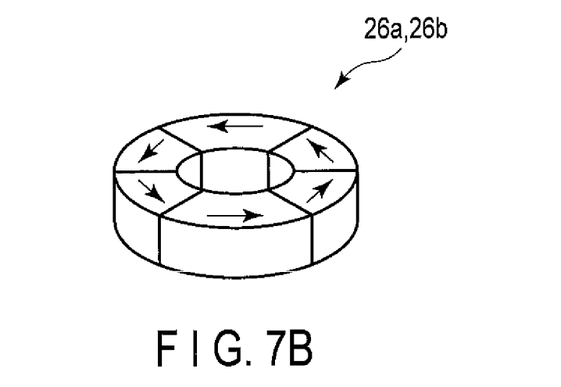
FIG. 7B is a view illustrating a concept of an example of a 6-division transducer as the ultrasonic transducer.
Figure 7C:
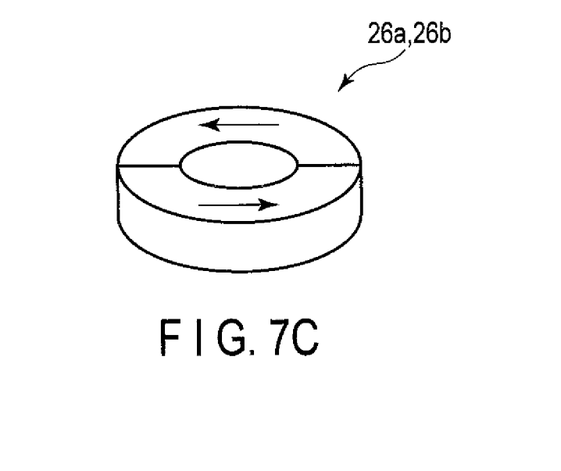
FIG. 7C is a view illustrating a concept of an example of a 2-division transducer as the ultrasonic transducer.

Next, referring to FIG. 5 and FIG. 6, the normal abrasion mode and cartilage abrasion mode by ultrasonic vibration of the ultrasonic treatment instrument will be described. FIG. 5 is a view which conceptually illustrates a configuration example of the ultrasonic transducer unit 12 of the handpiece 4. FIG. 6 is a view illustrating a concept for explaining the configuration of a handpiece body and the generation of ultrasonic vibration by an ultrasonic transducer. In addition, FIG. 7A is a view for explaining the generation of vibration by polarization of the ultrasonic transducer. FIG. 7B is a view illustrating a concept of an example of a 6-division transducer as the ultrasonic transducer. FIG. 7C is a view illustrating a concept of an example of a 2-division transducer as the ultrasonic transducer. In the description below, it is assumed that the probe 7 includes the treatment section 7*a* including the edge portion 7*c* composed of the grooves 7*b* as illustrated in FIG. 3.

As illustrated in FIG. 5 and FIG. 6, the ultrasonic transducer unit 12 of this embodiment is provided with a first ultrasonic transducer 26 and a second ultrasonic transducer 27 which are continuously arranged from the probe side in a handpiece body 25. The first ultrasonic transducer 26 generates longitudinal ultrasonic vibration which extends and contracts in the longitudinal direction m of the probe 7. The second ultrasonic transducer 27 generates ultrasonic vibration which is repetitive rotation, i.e. twisting vibration, in a direction crossing the longitudinal direction. The ultrasonic transducers, which generate ultrasonic vibrations of such longitudinal vibration and twisting vibration, have already been realized by publicly known piezoelectric elements. As illustrated in FIG. 6, the probe 7, which propagates ultrasonic vibration, generates longitudinal vibration by being fastened by screwing at the position of a point a at an apex of amplitude, and by being fixed to the handpiece body 25.

In the present embodiment, in FIG. 5 and FIG. 6, although the first ultrasonic transducer 26 which generates longitudinal vibration is arranged from the probe side, and subsequently the second ultrasonic transducer 27 which generates twisting vibration is arranged in this order, but the order of arrangement may be reversed. The second ultrasonic transducer 27 which generates twisting vibration may be arranged from the probe side, and subsequently the first ultrasonic transducer 26 which generates longitudinal vibration may be arranged in this order.

The first ultrasonic transducer 26 is an ultrasonic transducer which is normally used and generates longitudinal vibration. In addition, the second ultrasonic transducer 27 is an ultrasonic transducer which generates twisting vibration in the rotational direction. In this case, as illustrated in FIG. 7A, if voltage is applied to a fan-shaped piezoelectric element 26c, which is one of six divisions of the circumference, polarization occurs as indicated by an arrow. A twist as a whole is generated by a configuration in which fan-shaped piezoelectric elements 26c are annularly arranged so as to be polarized in the same circumferential direction, as illustrated in FIG. 7B. In addition, as illustrated in FIG. 7C, the piezoelectric element 26a, 26b can cause the same function, even with two divisions other than the six divisions.

If ultrasonic vibration of longitudinal vibration by the first ultrasonic transducer 26 is transmitted to the proximal end of the probe 7, the edge portion 7c of the probe 7, which is illustrated in FIG. 3A and FIG. 3B, vibrates. At this time, the groove 7b and edge 7d correspond to the vicinity of an antinode of vibration, and vibrate in a manner to reciprocally move along the longitudinal direction m. At this time, the vibration direction of longitudinal vibration is a direction perpendicular or substantially perpendicular to the edge 7d. The longitudinally vibrated edge portion 7c beats, pushes and pulls the treated target part, and mechanically abrades the treated target part.

Further, in the edge portion 7c, frictional heat is substantially generated between the edge portion 7c and the treated target part, and dissolutive abrasion is also performed, although the ratio in the abrasion amount is small, compared to the mechanical abrasion. The abrasion using the longitudinal vibration is the above-described normal abrasion mode which abrades all treated target parts, i.e. a biological tissue, a cartilage and a bone.

Besides, if ultrasonic vibration of twisting vibration by the second ultrasonic transducer 27 is transmitted to the proximal end of the probe 7, the edge portion 7c of the probe 7, which is illustrated in FIG. 3A and FIG. 3B, vibrates. At this time, the groove 7b and edge 7d vibrate in a manner to reciprocally move in a direction crossing the longitudinal direction m, and generates twisting vibration. At this time, the vibration direction of twisting vibration is a direction parallel or substantially parallel to the edge 7d. This twisting vibration is in the same direction as the direction of extension of the groove 7b and edge 7d. Hence, the edge portion 7c does not contribute to mechanical abrasion, and the surface of the probe 7 is only rubbed on the treated target part. Thus, the hammering function by beating hardly occurs. Specifically, the edge portion 7c generates frictional heat between itself and the cartilage by ultrasonic vibration, the temperature of the cartilage is raised to a proper temperature for dissolution of the cartilage, and the edge portion 7c abrades the cartilage. This abrasion using the twisting vibration is the above-described cartilage abrasion mode which abrades the cartilage among the treated target parts.

Although the example was described in which in the normal abrasion mode and cartilage abrasion mode, the vibration occurs in the direction perpendicularly crossing the direction of extension of the edge 7d, or vibrates in the direction parallel to the direction of extension of the edge 7d. However, the relationship of angles is not limited to this.

When the surgeon wishes to abrade the cartilage more than in the normal abrasion mode and also wishes to abrade the bone to some degree, the vibration may be reciprocal vibration in an oblique direction. The vibration in the oblique direction can be implemented by simultaneously driving the first ultrasonic transducer 26 and second ultrasonic transducer 27, and by adjusting the ratio of driving between them.

As regards the angle of the oblique vibration, for example, 45° to the direction of extension of the edge 7d may be used as a boundary. When vibration occurs at an inclination greater than 45°, this vibration may be classified as the mechanical abrasion by the normal abrasion mode in which the hammering effect is dominant. When vibration occurs at an inclination less than 45°, this vibration may be classified as the dissolutive abrasion by the cartilage abrasion mode in which heat is dominant. Specifically, in the present embodiment, the abrasion mode may be selected by using 45° to the direction of extension of the edge 7d as the reference. This classification of modes by angles is applicable to not only the present embodiment but also a second embodiment to be described later.

An abrasion treatment by the ultrasonic treatment instrument 1 including the probe 7, which is provided with the treatment section 7a with this configuration, will be described.

To begin with, in order to form a port for an arthroscope by cutting and opening a biological tissue, the surgeon operates the operation input unit 6 of the handpiece 4 or the footswitch 11, and sets the normal abrasion mode. Thereafter, the surgeon drives the first ultrasonic transducer 26, causes the probe 7 to generate ultrasonic vibration of the above-described longitudinal vibration, and pushes the edge portion 7c of the treatment section 7a on the biological tissue which is the treated target. The edge portion 7c mechanically abrades the biological tissue, and cuts and opens the biological tissue until the cartilage (degenerated cartilage) is exposed. In the mechanical abrasion by the normal abrasion mode, when cutting and opening have reached the cartilage, the abrasion speed decreases due to the elasticity of the cartilage. Thus, the cutting-and-opening treatment is stopped by ascertaining whether the cartilage is exposed or not, based on the variation in speed. At this time, even if the temperature of the probe 7 has increased, it is assumed that the increase is mainly due to the function of mechanical abrasion.

Next, at a time of starting the abrasion treatment of the exposed cartilage, the surgeon operates the operation input unit 6 of the handpiece 4 and changes the normal abrasion mode to the cartilage abrasion mode. By driving the second ultrasonic transducer 27, the surgeon causes the probe 7 to generate ultrasonic vibration of the above-described twisting vibration, and pushes the edge portion 7c of the treatment section 7a on the cartilage of the treated target. Frictional heat due to the twisting vibration occurs in the cartilage to which the edge portion 7c is applied, and the cartilage is heated. The temperature of the cartilage rises to about 120° C. to 160° C. as described above, and the cartilage is dissolutively abraded and a subcartilaginous bone is exposed.

As described above, although the temperature of the edge portion 7c, which generates twisting vibration, is high, the mechanical abrasion does not function. Thus, the abrasion speed decreases, the repulsion to pushing increases due to the rigidity of the bone, and it is understood that the subcartilaginous bone has been exposed. Thereafter, the driving of the second ultrasonic transducer 27 is stopped, and the cartilage abrasion mode is finished.

Next, the surgeon operates the operation input unit 6 once again, changes the cartilage abrasion mode to the normal abrasion mode, transmits ultrasonic vibration of longitudinal vibration to the probe 7, and mechanically abrades the subcartilaginous bone by the edge portion 7c of the treatment section 7a.

As described above, the ultrasonic treatment instrument 3 of the present embodiment has the cartilage abrasion mode which abrades the cartilage and the normal abrasion mode which abrades the biological tissue, cartilage and subcartilaginous bone, such that these modes can be switched depending on the treated target part. In the setting of the normal abrasion mode, the judgment of switching from the biological tissue to cartilage is easy. In addition, in the setting of the cartilage abrasion mode, only the cartilage can be abraded by dissolutively abrading the cartilage, and the abrasion is stopped, and thus damage to the subcartilaginous bone can be avoided. Accordingly, the ultrasonic treatment instrument 3 of the present embodiment can easily cut and divide the biological tissue, cartilage and bone (e.g. subcartilaginous bone) with low invasion.

Next, a modification of the first embodiment will be described with reference to FIG. 4A and FIG. 4B.

FIG. 4 illustrates, as the modification of the first embodiment, a configuration example of a treatment section 31a provided in a probe 31 in the ultrasonic treatment instrument 3. In the present modification, the direction of the groove (edge) of the edge portion provided in the treatment section is different from the direction in the above-described first embodiment. The other structural parts are the same as in the first embodiment, and a detailed description thereof is omitted here.

As illustrated in FIG. 4, in the treatment section 31a of this modification, an edge 31d formed by a groove 31b of an edge portion 31c is formed to extend in the longitudinal direction m of the probe 31. The edge portion 31c has the same advantageous effects as the edge portion 7c formed to extend in the direction n crossing the longitudinal direction m of the treatment section 7a of the above-described first embodiment, and the direction in which the edge functions is different.

Figure 4A:
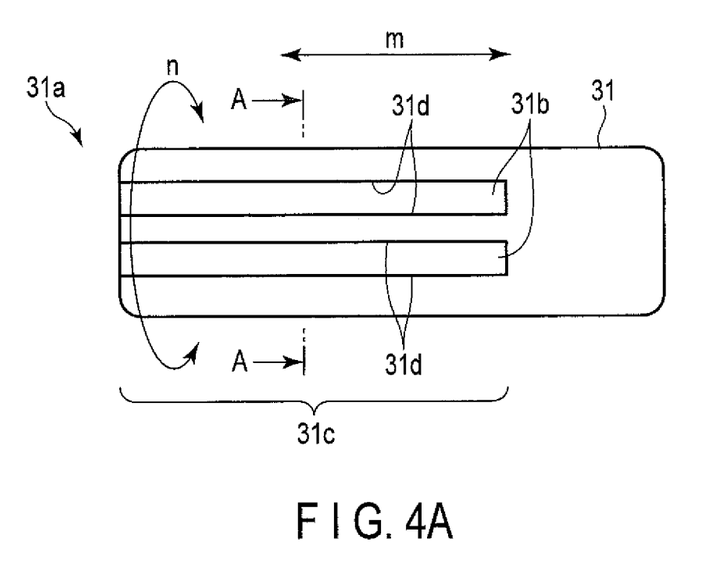
FIG. 4A is a view illustrating a conceptual external appearance configuration of a treatment section, as viewed from a front surface side, which is provided in a probe in a modification of the first embodiment.
Figure 4B:
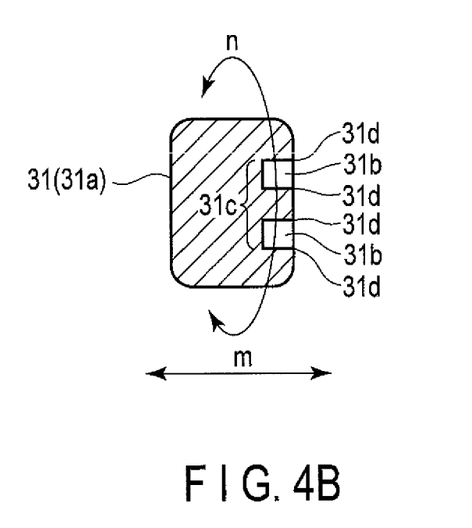
FIG. 4B is a view illustrating a cross-sectional configuration along line A-A of the treatment section provided in the probe illustrated in FIG. 4A.

In the present modification, when the ultrasonic vibration of longitudinal vibration by the above-described first ultrasonic transducer 26 is applied to the edge portion 31c of the probe 31 illustrated in FIG. 4A and FIG. 4B, vibration occurs such that the edge 31d reciprocally moves in the longitudinal direction m. Since this longitudinal vibration is in the same direction as the direction of extension of the groove 31b of the edge portion 31c, the edge 31d of the edge portion 31c does not contribute to mechanical abrasion, and the surface of the probe 31 is only rubbed on the treated target part. Thus, the hammering function by beating hardly occurs. Specifically, the edge portion 31c generates frictional heat by ultrasonic vibration, the temperature of the cartilage is raised to a proper temperature for dissolution of the cartilage, and the edge portion 31c abrades the cartilage. This abrasion using the longitudinal vibration is the above-described cartilage abrasion mode which abrades the cartilage among the treated target parts.

In addition, when the ultrasonic vibration of twisting vibration by the second ultrasonic transducer 27 is applied to the edge portion 31c of the probe 31 illustrated in FIG. 4A and FIG. 4B, the groove 31b and edge 31d reciprocally rotate in the direction n crossing the longitudinal direction m, and generates twisting vibration. In this twisting vibration, the edge 31b beats and rotates the treated target part, and mechanically abrades the treated target part.

Further, in the edge portion 31c, frictional heat, too, is substantially generated between the edge portion 31c and the treated target part, and dissolutive abrasion is also performed, although the ratio in the abrasion amount is small, compared to the mechanical abrasion. The abrasion using this twisting vibration is the above-described normal abrasion mode which abrades all treated target parts, i.e. a biological tissue, a cartilage and a bone.

As described above, in the above-described first embodiment and modification, the angle (horizontal or perpendicular) of contact of the edge with the treated target part is reversed at the time of longitudinal vibration or at the time of twisting vibration. Thus, the ultrasonic transducer 26, 27, which is driven in the normal abrasion mode and cartilage abrasion mode, is different. Specifically, in the normal abrasion mode, the second ultrasonic transducer 27, in which the probe 31 is caused to generate twisting vibration, is driven. In the cartilage abrasion mode, the first ultrasonic transducer 26, in which the probe 31 is caused to generate longitudinal vibration, is driven.

According to the present modification, the same advantageous effects as in the above-described first embodiment can be obtained. In the normal abrasion mode, the judgment of switching from the biological tissue to cartilage is easy. In addition, in the setting of the cartilage abrasion mode, only the cartilage can be abraded by dissolutively abrading the cartilage, and the abrasion is stopped, and thus damage to the subcartilaginous bone can be avoided.

Accordingly, the ultrasonic treatment instrument 3 of the present embodiment can easily cut and divide the biological tissue, cartilage and bone (e.g. subcartilaginous bone) with low invasion.

Second Embodiment

Figure 8A:
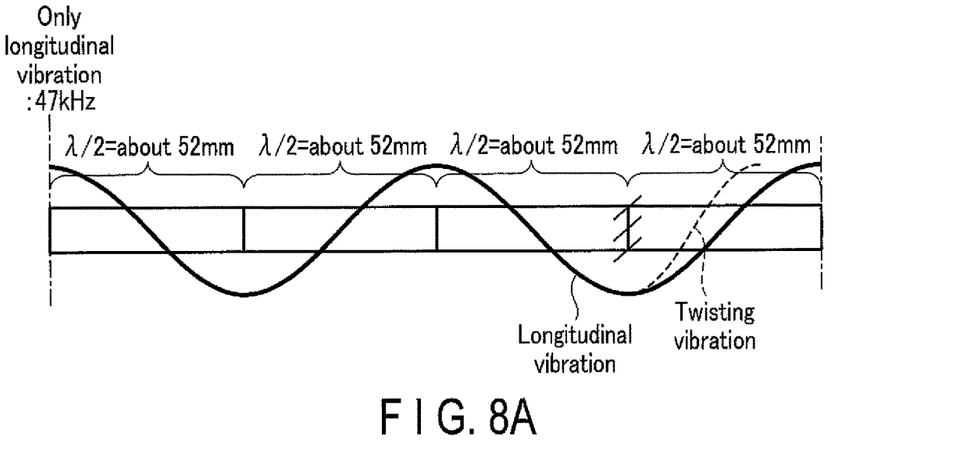
FIG. 8A is a view for explaining longitudinal vibration which is generated by an ultrasonic transducer of an ultrasonic treatment instrument according to a second embodiment.
Figure 8B:
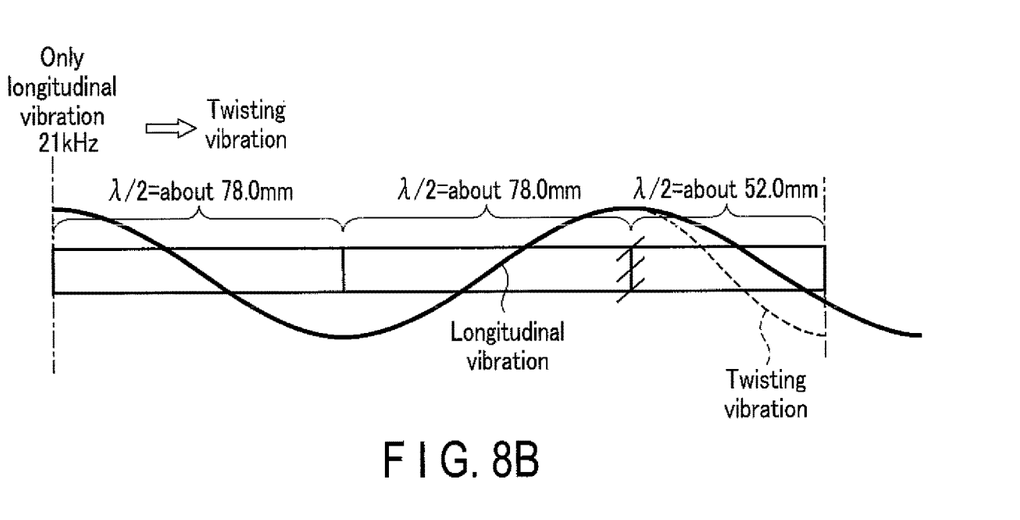
FIG. 8B is a view for explaining twisting vibration which is generated by the ultrasonic transducer of the ultrasonic treatment instrument according to the second embodiment.
Figure 9A:
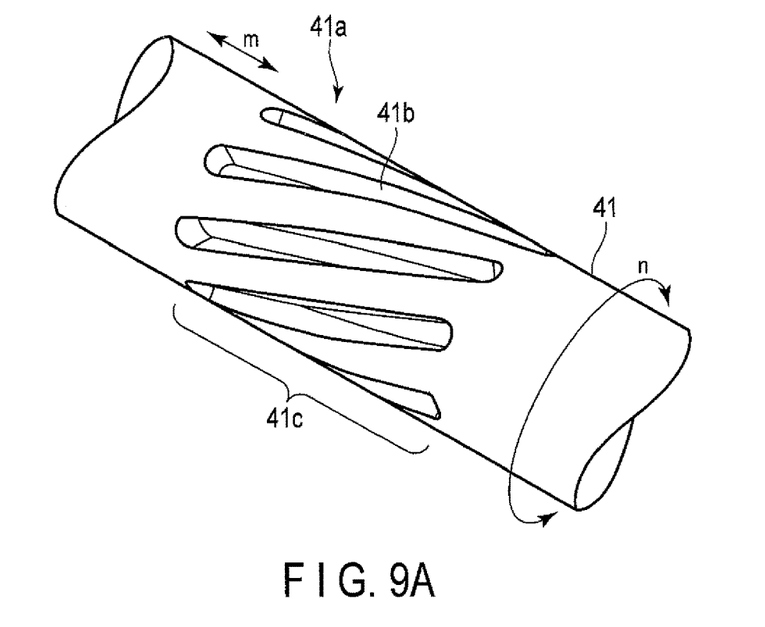
FIG. 9A is a perspective view illustrating an external appearance configuration of a treatment section provided in a probe in the second embodiment.
Figure 9B:
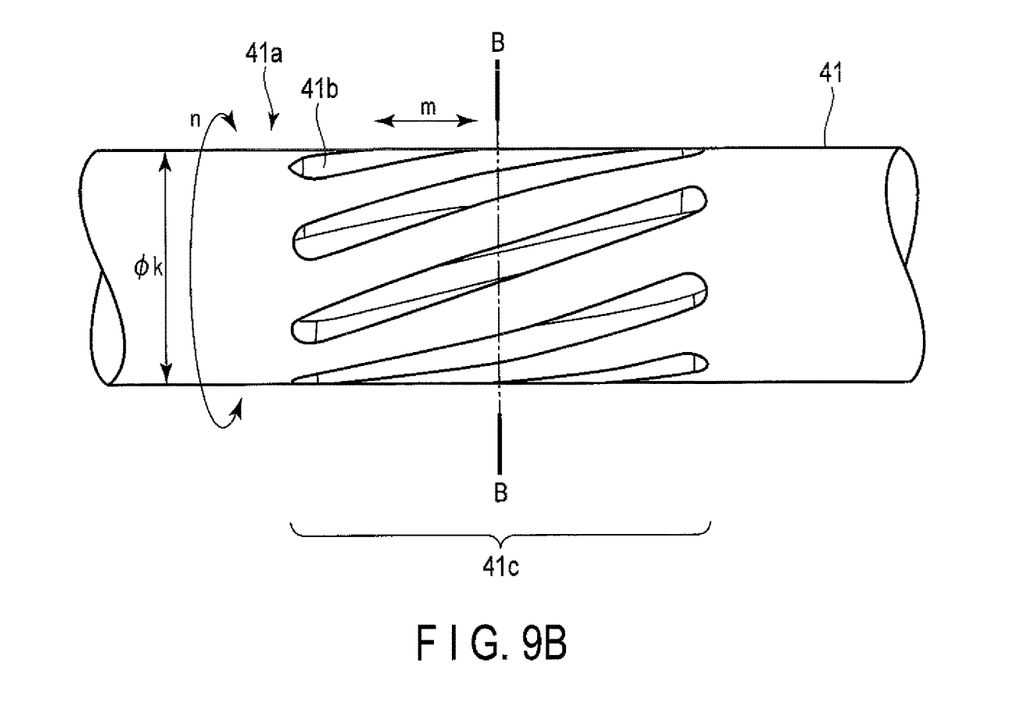
FIG. 9B is a view illustrating an external appearance configuration of the treatment section, as viewed from a front surface side, which is provided in the probe in the second embodiment.
Figure 9C:
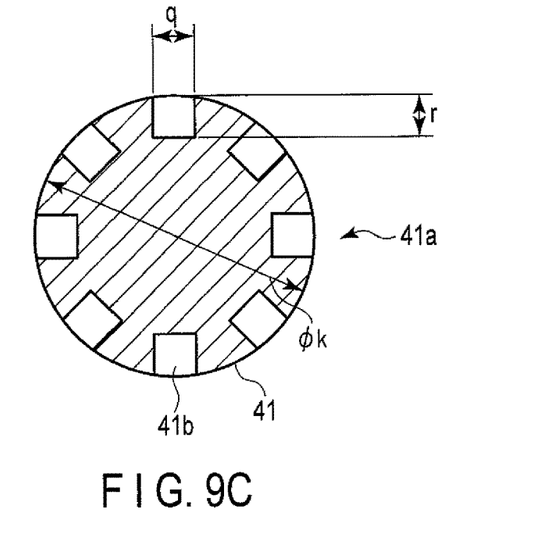
FIG. 9C is a view illustrating a cross-sectional configuration along line B-B of the treatment section provided in the probe illustrated in FIG. 9B.
Figure 9D:
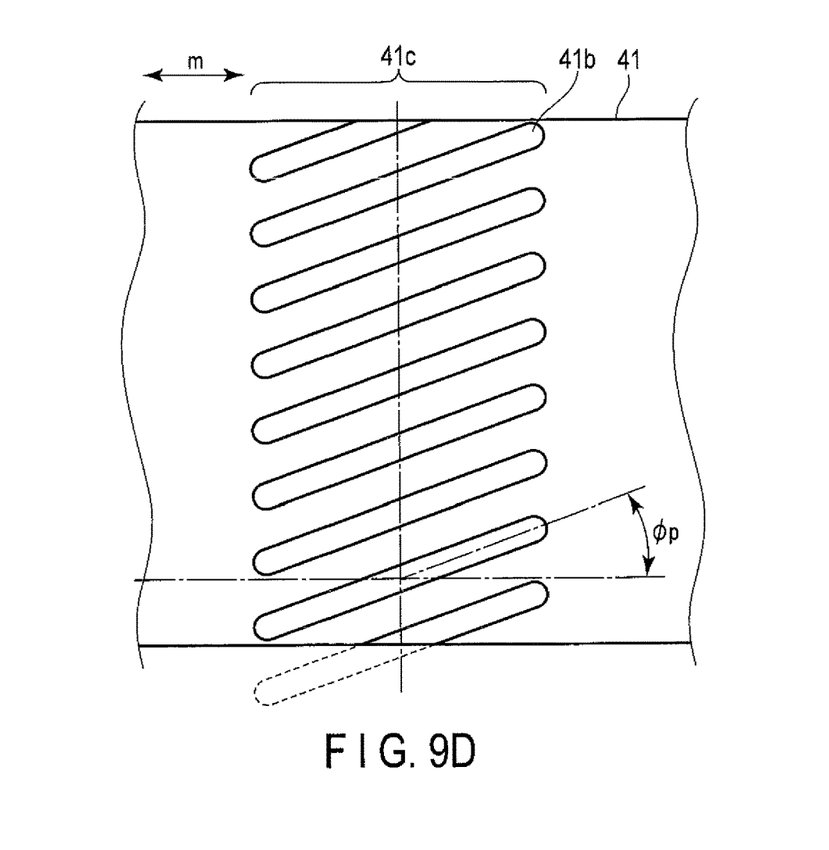
FIG. 9D is a development of the treatment section provided in the probe in the second embodiment.

Next, an ultrasonic treatment instrument for articulations according to a second embodiment of the present invention will be described with reference to FIG. 8A and FIG. 8B. FIG. 8A is a view for explaining longitudinal vibration which is generated by an ultrasonic transducer. FIG. 8B is a view for explaining twisting vibration which is generated by the ultrasonic transducer. FIG. 9A is a perspective view illustrating an external appearance configuration of a twisting groove provided in a probe. FIG. 9B is a view illustrating an external appearance configuration of the twisting groove, as viewed from a front surface side, which is provided in the probe. FIG. 9C is a view illustrating a cross-sectional configuration along line B-B of the twisting groove provided in the probe illustrated in FIG. 9B. FIG. 9D is a development of the twisting groove provided in the probe.

The above-described first embodiment has the configuration which includes the ultrasonic transducer 26 that generates longitudinal vibration and the ultrasonic transducer 27 that generates twisting vibration (see FIG. 5 to FIG. 7C).

By contrast, the present embodiment has such a configuration that a plurality of twisting grooves 41b illustrated in FIG. 9A and FIG. 9B are formed on an intermediate portion of the probe, and the vibration frequency is varied by a single ultrasonic transducer, thereby generating longitudinal vibration and twisting vibration. When the frequency is varied by the single ultrasonic transducer, various methods, such as varying an input signal to the transducer, can be used.

To begin with, the twisting groove 41b is described.

As illustrated in FIG. 9A and FIG. 9B, the twisting grooves 41b are twisting grooves which extend in a direction inclined to the longitudinal direction of a probe 41 and are formed equidistantly along a circumferential surface of the probe 41. As illustrated in FIG. 9D, the grooves 41b are set, for example, at an inclination angle Φp=20° with respect to the longitudinal direction m. As illustrated in FIG. 9C, the grooves 41b are arranged equidistantly over the entire circumference. The probe 41 has a diameter that is equal to the diameter of the probe 7, and is, for example, Φk=about 6 to 7 mm. In addition, in the case of this probe diameter, each of the width q and depth r of the groove 41b is preferably about 1 mm. Needless to say, the values of the width and depth are not limited.

When the inclination angle Φp at the edge of the twisting groove 41b is parallel to the vibration direction of the probe 41, the function of mechanical abrasion is small, and the function of mechanical abrasion becomes greater as the angle Φp becomes closer to 90° C. In addition, the function of dissolutive abrasion is in an opposite relationship to the function of mechanical abrasion. When the inclination angle Φp is parallel to the vibration direction of the probe 41, the function of dissolutive abrasion is large, i.e. the temperature of friction is high. As the inclination angle Φp becomes closer to 90° C., the function of mechanical abrasion becomes smaller, i.e. the temperature of friction is lower. Accordingly, the inclination angle Φp is properly set according to design specifications, etc., based on the treated target parts and the content of treatment. In addition, the grooves 41b formed on the probe 41 do not need to be arranged equidistantly, and the intervals may be increased or decreased, as needed.

In the configuration for generating longitudinal vibration and twisting vibration in this embodiment, the length of the probe is set to an integral multiple of ½ wavelength or (first wavelength) of one preset ultrasonic vibration. Thereby, longitudinal vibration occurs at the distal end of the probe which propagates vibration of this first wavelength. Twisting vibration occurs at the distal end of the probe which propagates vibration of a wavelength (second wavelength) other than this first wavelength.

In order to confirm the generation of these vibrations, for example, as illustrated in FIG. 8A, the length of the probe 7 from the ultrasonic transducer is set at 208 mm here, in accordance with an integral multiple of the oscillation frequency (wavelength of longitudinal vibration: ½ wavelength (λ/2)=about 52 mm) of vibration that is used. In this configuration, a twisting groove 41b, which is indicated by oblique lines, is formed at a position of ½ wavelength from the distal side of the probe.

Next, for example, when vibration is generated at a vibration frequency of 47 kHz, the wavelength of twisting vibration does not agree with the length of the probe 7, and the wavelength of longitudinal vibration agrees with the length of the probe 7, on the forward side of the slit indicated by oblique lines. Thus, in the case of the oscillation frequency of 47 kHz, longitudinal vibration is transmitted. In addition, at this time, twisting vibration does not occur.

Besides, as illustrated in FIG. 8B, when the length of the probe 7 from the ultrasonic transducer is similarly set to 208 mm, and vibration is generated at a vibration frequency of, e.g. 21 kHz, ½ wavelength (λ/2) of longitudinal vibration becomes about 78 mm. On the forward side of the twisting groove 41b indicated by oblique lines, the wavelength of twisting vibration agrees with the length of the probe 7, and the antinode position of vibration corresponds to the distal end of the probe 7. Thus, in the case of the vibration frequency of 21 kHz, twisting vibration occurs. At this time, the amplitude of longitudinal vibration is suppressed at the position of the distal end of the probe 7.

Accordingly, by varying the oscillation frequency, i.e. wavelength, of ultrasonic vibration which one ultrasonic transducer oscillates, if the wavelength of a certain vibration frequency agrees with the length of the probe 7, twisting vibration mainly occurs, and if the wavelength of the certain vibration frequency does not agree with the length of the probe 7, longitudinal vibration mainly occurs.

From the above, according to the present embodiment, the same advantageous effects as in the above-described first embodiment can be obtained. Moreover, by making the length from the distal end of the probe to the slit agree with the oscillation frequency, i.e. the wavelength, of ultrasonic vibration oscillated by the ultrasonic transducer, the twisting vibration or longitudinal vibration can selectively be generated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An ultrasonic treatment system for articulations, comprising an ultrasonic treatment instrument configured to perform a treatment on an articulation by using ultrasonic vibration, and a driving control device configured to control driving by the ultrasonic vibration, the ultrasonic treatment instrument comprising:
a probe including a distal portion and a proximal portion and configured to transmit ultrasonic vibration, the probe being configured such that a length from the distal portion to the proximal portion is set to be equal to an integral multiple of ½ wavelength which is a first wavelength of one preset ultrasonic vibration, and a slit formed at a position of ½ wavelength from the distal portion;
a treatment section provided at the distal portion of the probe and configured to perform a treatment on a treated target part; and
a first ultrasonic transducer configured to transmit ultrasonic vibration to the treatment section, and the driving control device comprising:
a driving control unit configured to transmit to the first ultrasonic transducer a driving signal which causes the first ultrasonic transducer to generate ultrasonic vibration with at least two different frequencies,
the driving control unit being configured to cause the probe to generate longitudinal vibration by applying to the first ultrasonic transducer a driving signal of an oscillation frequency of an integral multiple of the first wavelength, and configured to cause the probe to generate twisting vibration by applying to the first ultrasonic transducer a driving signal of an oscillation frequency other than the oscillation frequency of the integral multiple of the first wavelength.

2. An ultrasonic treatment instrument for articulations which is configured to perform a treatment on an articulation by using ultrasonic vibration, comprising:
a probe including a distal portion and a proximal portion and configured to transmit the ultrasonic vibration;
a treatment section provided at the distal portion of the probe and configured to perform a treatment on a treated target part;
an edge provided on the treatment section and extending in a direction substantially perpendicular to, or in a direction parallel to, a longitudinal direction extending from the distal portion to the proximal portion of the probe;
a first ultrasonic transducer configured to generate ultrasonic vibration in a direction crossing the direction in which the edge extends;
a second ultrasonic transducer configured to generate ultrasonic vibration in a direction parallel to the direction in which the edge extends; and
a vibration input unit configured to cause the treatment section to vibrate by varying a vibration frequency, the vibration input unit being configured to simultaneously drive the first ultrasonic transducer and the second ultrasonic transducer and to cause the first ultrasonic transducer and the second ultrasonic transducer to generate twisting vibration, such that when vibration occurs at an inclination greater than 45° with respect to the direction in which the edge extends, mechanical abrasion is performed by the treatment section, and when vibration occurs at an inclination less than 45° with respect to the direction in which the edge extends, dissolutive abrasion is performed by the treatment section.

3. The ultrasonic treatment instrument for articulations of claim 2, wherein the first ultrasonic transducer is configured to generate longitudinal vibration in which vibration occurs in a direction parallel to a longitudinal direction of the probe,
the second ultrasonic transducer is configured to generate twisting vibration in which vibration occurs in a direction crossing the longitudinal direction of the probe,
the edges include at least one of a first edge formed in a groove shape extending in a direction parallel to the longitudinal direction of the probe, and a second edge formed in a groove shape extending in a direction crossing the longitudinal direction of the probe, and
the ultrasonic treatment instrument for articulations further comprises an operation input unit configured to instruct driving of one of the first ultrasonic transducer and the second ultrasonic transducer, and configured to switchably select a normal abrasion mode which causes the probe to vibrate in a direction crossing the direction in which the edge extends and executes mechanical abrasion by beating treated target parts including a cartilage and a bone by transmission of ultrasonic vibration, and a cartilage abrasion mode which causes the probe to vibrate in a direction parallel to the direction in which the edge extends, causes the treatment section that is in contact with a cartilage to generate heat by transmission of ultrasonic vibration, and dissolutively abrades the cartilage.

4. An ultrasonic treatment system for articulations, comprising:
the ultrasonic treatment instrument for articulations of claim 2; and
a driving controller configured to transmit a driving signal, which drives an ultrasonic transducer, to the first ultrasonic transducer or the second ultrasonic transducer.

5. The ultrasonic treatment system for articulations of claim 1, wherein an edge of the treatment section is provided in such a position that the edge extends in a direction substantially perpendicular to, or in a direction parallel to, a longitudinal direction of the probe.

* * * * *